United States Patent [19]
Litchholt

[11] Patent Number: 5,636,414
[45] Date of Patent: Jun. 10, 1997

[54] TWO MECHANISM MECHANICAL FASTENER

[76] Inventor: John J. Litchholt, 101 Hopping Ct., Harrison, Ohio 45030

[21] Appl. No.: 432,408

[22] Filed: Feb. 24, 1995

[51] Int. Cl.$^6$ ........................................... A44B 18/00
[52] U.S. Cl. ............................................. 24/304; 24/306
[58] Field of Search ................. 24/304, 306, DIG. 11; 604/389, 391

[56] References Cited

U.S. PATENT DOCUMENTS

| | | | |
|---|---|---|---|
| 3,176,364 | 4/1965 | Dritz | 24/306 X |
| 3,574,864 | 4/1971 | Bradley | 2/114 |
| 4,054,952 | 10/1977 | Swallow | 2/338 |
| 4,074,397 | 2/1978 | Rosin | 24/73 AS |
| 4,239,829 | 12/1980 | Cohen | 24/DIG. 11 |
| 5,019,065 | 5/1991 | Scripps | 604/385.1 |
| 5,085,655 | 2/1992 | Mann et al. | 604/389 |
| 5,180,534 | 1/1993 | Thomas et al. | 264/145 |
| 5,196,000 | 3/1993 | Clear et al. | 604/385.2 |
| 5,221,276 | 6/1993 | Battrell | 24/304 |
| 5,325,569 | 7/1994 | Goulait et al. | 24/448 |
| 5,326,415 | 7/1994 | Thomas et al. | 156/244.11 |
| 5,476,702 | 12/1995 | Datta et al. | 428/99 |

Primary Examiner—James R. Brittain
Attorney, Agent, or Firm—Marshall, O'Toole, Gerstein, Murray & Borun

[57] ABSTRACT

An economical, reusable primary two mechanism fastener system useable with disposable absorbent products is provided. The fastening system comprises a first and second fastening portion. The first fastener portion comprises a hook fastening material and a first cohesive portion. The second fastening portion comprises a nonwoven fibrous portion engageable with the hook fastening material and a second cohesive portion engageable with the first cohesive portion. The hook fastening material has base and hook surface areas. Various embodiments of the first fastening portion include the first cohesive portion being coated on a portion of the hook fastening material. For example, the cohesive may be coated on the base surface area alone, the hook surface area alone or a portion of both the hook and surface area portions. The amount, type and manner of applying the cohesive in addition to the type and basis weight of the nonwoven material can be varied to obtain the desired shear and peel force resistance for the engaged fastener.

7 Claims, 4 Drawing Sheets

TWO MECHANISM MECHANICAL FASTENER

FIELD OF THE INVENTION

The present invention relates to a dual mechanism mechanical fasteners which can be repeatedly fastened and unfastened. The invention also relates to articles, especially disposable absorbent articles, for which the fasteners are particularly useful.

BACKGROUND OF THE INVENTION

Disposable absorbent articles such as disposable diapers are well-known articles of manufacture which are worn by infants and incontinent persons. Disposable diapers are worn about the lower torso of the wearer and are intended to absorb and contain urine and other body exudates thereby preventing these exudates from soiling, wetting, or otherwise contaminating the articles (e.g. clothing, bedding, etc.) which come into contact with the diaper wearer.

When using a disposable diaper, the diaper user fits the diaper on the wearer and fastens it about the wearer's waist by a primary fastening system to thereby effect a side closure. Fitting the diaper about the wearer usually requires the front and back waist portions of the diaper to overlap each other. Since proper and sustained fit about the waist and legs of the wearer is vital for optimal performance in terms of minimizing leakage of body exudates out of the diaper, a diaper fastening system must be able to provide an effective side (or primary) closure in which the front and back waist portions are maintained in an overlapping configuration. As the diaper is worn, forces tend to cause the overlapping portions to shift position relative to each other. In other words, the overlapping portions are subjected to forces which tend to cause the portions to assume a position relative to each other which is different from the position they assume when the diaper is initially fitted to the wearer. Unless such shifting is limited, the fit and containment characteristics of the diaper are degraded as the diaper is worn. Thus, the fastening system must be designed to securely engage so it does not separate due to the peel forces and shear stress encountered by the fastening system during use.

As used herein, the "primary fastening system" refers to a system which provides the principal means for engaging and disengaging an article to be worn about a wearer. In the case of an absorbent article, such as a diaper, the primary fastening system operates as the side closure means which attaches the absorbent article about the wearer and provides a variable side closure to maintain the diaper on the wearer. This is to be distinguished from the waist closure fastening system described in U.S. Pat. No. 5,196,000 which is used in addition to a primary fastening system to provide lateral tension in order to prevent gapping, sagging, and rollover of the elasticized waistband. A primary fastening system encounters different amounts of shear and peel forces than such a waist closure system does and therefore must be designed differently to adequately resist those forces.

As used herein, the term "shear stress" refers to the distributed forces acting tangentially to the surface of contact of the members of the fastening system (or along the x/y plane). During the wearing of a diaper, shear stress tends to cause the members of the fastening system to shift with respect to each other. Shear stress is to be distinguished from "peel forces" which act on the members of the fastening system so as to separate and disengage from each other (in the z direction). A disposable diaper is typically subjected to peel forces in at least three ways. Peel forces are generated by the movements of the wearer during use as they tend to cause the first and second members of the fastening system to pull away from each other, by the wearer in trying to unfasten the fastening system during wear (this being a special problem for disposable diapers worn by infants because infants should not be able to unfasten and remove the diaper on their own), and by the user to check the diaper for soiling or to remove the diaper from the wearer. Because the fastening system should be able to be checked and removed by the user and because the user generated peel forces are much higher than the peel forces generated by the first two methods, the fastening system is preferably designed to have a resistance to peel forces (peel force resistance) with respect to only the movement and wearer generated methods. Therefore, the peel resistance should only be great enough to prevent failure of the fastening system during the first two methods but low enough to allow the user to check the diaper for soiling or to remove the diaper from the wearer without undue difficulty or tearing of other members of the diaper.

Therefore, it is desirable to design a primary fastening system capable of resisting shear stress and peel forces generated by the wearer but having a peel force resistance low enough to allow the user to easily remove the diaper or check the diaper for soiling.

Typically, fastening systems have been provided which have adequate shear force resistance to prevent the panels from shifting with respect to each other. However, because the shear forces are so high, the peel resistance of the fastening system is also very high. This is generally the situation because as the coat weight of the adhesive on the smooth surface of the backing web of the fastener is increased to improve the shear force resistance of the fastener, the peel force resistance also rapidly increases. The result is that typical fastening systems may rip the backsheet of the diaper during the process of unfastening it to check if the diaper has been soiled or to adjust its fit, thereby leaving a hole in the backsheet of the diaper and rendering the fastener unrefastenable and the diaper unusable, due to the high peel resistance of the fastener.

Other primary fastening systems have been provided but suffer from one or more problems. For example, hook and loop fastening systems such as those available commercially as Velcro® have been employed but are very expensive and require specific male and female engagement portions. Combination mechanical/adhesive primary fastener systems such as shown in U.S. Pat. Nos. 4,946,527 and 5,196,000 have also been employed. These systems suffer from being costly, from requiring specific matching male and female engagement portions and from the possibility of the adhesive being rendered unuseable by contamination from oils, ointments and powders used during the diapering procedure.

Thus, it would be advantageous to provide an inexpensive primary fastening system capable of using a wide variety of male and female engagement portions, resistant to contamination, having a high enough shear resistance to prevent the panels from shifting with respect to each other and sufficient peel resistance to prevent failure of the fastening system by the wearer's movements but a peel resistance low enough to allow the user to easily remove the diaper and check for soiling or fit without rendering the fastening system unrefastenable or the diaper unuseable.

SUMMARY OF THE INVENTION

According to the present invention, an economical, reusable primary two mechanism fastener system is provided.

The fastening system comprises a first and second fastening portion. The first fastener portion comprises a hook fastening material and a first cohesive portion. The second fastening portion comprises a receiving material portion such as a nonwoven fibrous, or other suitable material engageable with the hook fastening material and a second cohesive portion engageable with the first cohesive portion. The hook fastening material has base and hook surface areas. Various embodiments of the first fastening portion include the first cohesive portion being coated on a portion of the hook fastening material. For example, the cohesive may be coated on the base surface area alone, the hook surface area alone or a portion of both the hook and surface area portions. The amount, type and manner of applying the cohesive in addition to the type and basis weight of the receiving material can be varied to obtain the desired shear and peel force resistance for the engaged fastener.

Further, the present invention relates to disposable absorbent articles, such as diapers, having a fastening system according to the present invention. The diaper fastening system affixes the overlapping portions of the diaper to each other and maintains them in contact with each other during use. The fastening system prevents separation of the overlapping waist portions because the fastening system is able to resist the wearer-generated peel forces encountered during wear and the shear stress encountered when the diaper is worn. Further, the fastening system allows the user to easily refasten and check the diaper for soiling and remove the diaper without rendering the fastening system unrefastenable or the diaper unuseable.

Further, the present invention relates to the method of fastening two objects together using the two mechanism fastener system

BRIEF DESCRIPTION OF THE DRAWINGS

The foregoing and other objects, features and advantages of the invention will be more apparent from the following detailed description of the invention, as illustrated in the accompanying figures of the drawings, in which like reference characters refer to the same parts throughout the different figures wherein.

Figure 1:
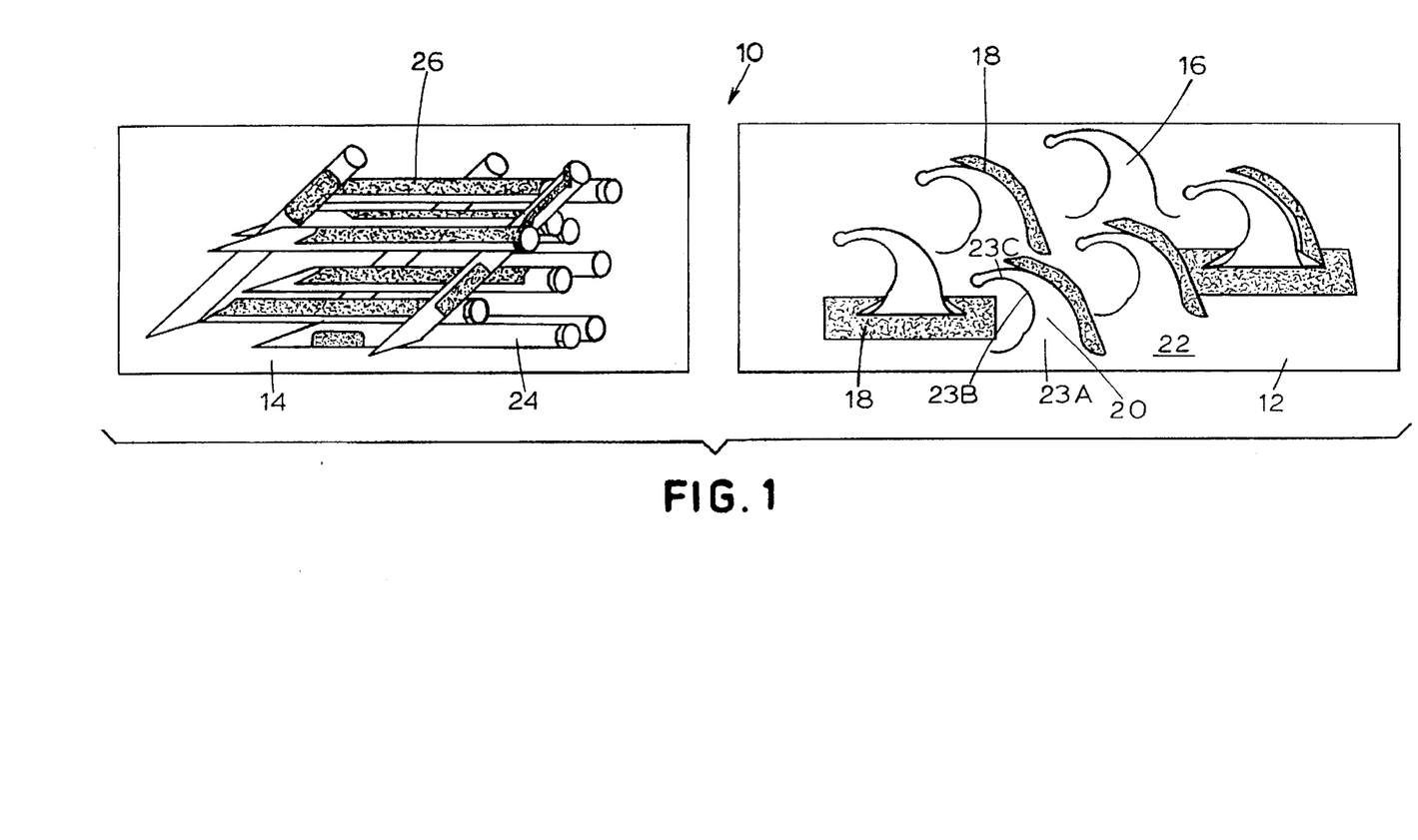
FIG. 1 is a schematic of a primary two mechanism fastening mechanism of the present invention.

The engaging elements 20 also have a portion 24A of the shank 23B and engaging portion 23C which are oriented toward or face the backing 22 and a portion 24D which is oriented or faces away from the backing 22.

DETAILED DESCRIPTION OF THE INVENTION

As seen in FIG. 1, a primary two mechanism mechanical fastener system 10 is provided. The fastener comprises a first fastener portion 12 and a second fastener portion 14. The first fastener portion 12 comprises hook fastening material 16 (a first mechanical fastener portion) and a first cohesive portion 18.

As used herein, the term "hook fastening material" is used to designate a material having engaging elements. Thus, the hook fastening material may also be referred to as a male fastener. It should also be understood that the use of the term "hook" should be non-limiting in the sense that the engaging elements may comprise any shapes as are known in the art so long as they are adapted to engage a complementary mechanical closure element such as a loop fastening material or another hook fastening material.

The hook fastening material 16 is preferably intended to mechanically engage a fibrous nonwoven or any other suitable material. Thus, a hook fastening material according to the present invention may be manufactured from a wide range of materials. Suitable materials include nylon, polyester, polypropylene, or any combination of these materials, or other materials as are known in the art. As seen in FIG. 1, a suitable hook fastening material comprises a number of shaped engaging elements 20 projection from a backing 22 such as the commercially available material designated "Scotchmate" brand No. FJ3402 available from Minnesota Mining and Manufacturing Company, St. Paul, Minn. As seen in FIG. 1, each engaging element has a base 23A connected to the backing 22, a shank 23B connected to the base 23A and an engaging portion 23C connected to the shank 23B and spaced from the base 23A. Alternatively, the engaging elements may have any shape such as hooks, "Ts", mushrooms, or any other shape that is well known in the art. Especially preferred are the hooks or prongs shown in U.S. Pat. No. 5,116,563 to Thomas et al. and U.S. Pat. No. 5,058,247 to Thomas et al., both of which are incorporated herein by reference.

The first cohesive portion 18 comprises a cohesive material. The term "cohesive material" refers to materials which only form a bond with other cohesives and generally will only strongly adhere to a like material. Cohesive materials comprise water base, hot melt, crosslinked and tackless cohesives or mixtures thereof. Preferably, a tackless cohesive is utilized. As discussed in greater detail below the first cohesive portion may be coated onto a portion of the surface area of the hook fastening material or a segregated area of the first fastener portion 12.

The second fastener portion 14 is complementary to the first fastener portion 12 and is comprised of a receiving material portion 24 (a second mechanical fastener portion) and a second cohesive portion 26. The receiving material portion 24 provides a plurality of fibrous or other elements that engage the engaging elements 20 of the hook fastening material 16. The receiving portion 24 is preferably a nonwoven material, such as a carded web or spun bond web nonwoven. The receiving portion 24 may also be a fibrous fabric including melt blown or flocked substrates. In addition, the receiving material portion 24 could alternatively be comprised of woven materials, reticulated foam, or perforated films capable of engaging the hook fastening material 16.

The second cohesive portion 26 is comprised of a cohesive material that is compatible and will form a bond or engage with the first cohesive portion 18. As seen in FIG. 1, the second cohesive portion 26 is coated on at least a portion of the nonwoven material 24. The second cohesive portion 26 is preferably comprised of the same cohesive material as the first cohesive portion 18.

As seen in FIGS. 2–5, various embodiments of the first fastener portion 212, 312, 412, 512 are shown. The hook fastening material 216, 316, 416, 516 and the cohesive 218, 318, 418, 518 are combined in several ways.

Figure 2:
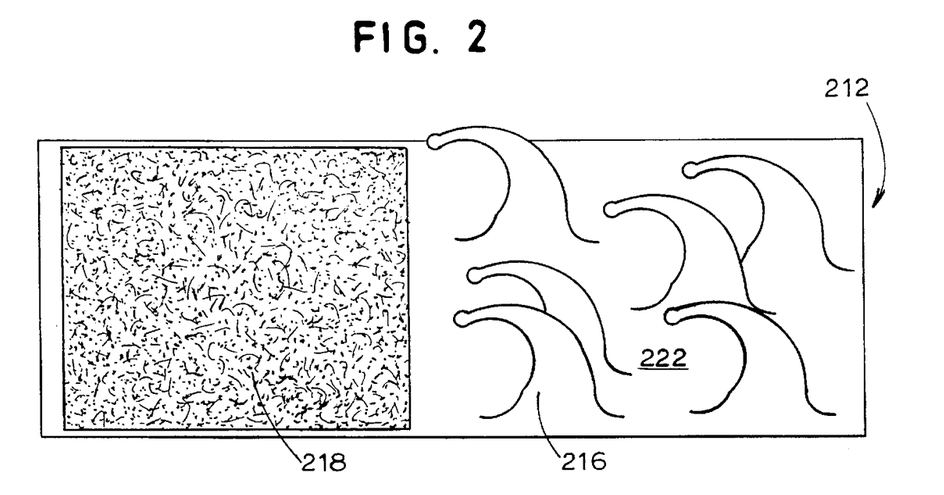
FIG. 2 is a schematic of a first embodiment of a first fastener portion of the present invention.

As seen in FIG. 2, a first fastener portion is provided where the cohesive portion 218 is not coated on the hook fastening material 216, but is segregated in a distinct patch away from the hook fastening material 216. The segregated cohesive portion 218 and the segregated hook fastening material 216 may be applied in a pattern such as shown in FIG. 2 or alternate segregated patterns such as stripes, checkerboards or other patterns.

Figure 3:
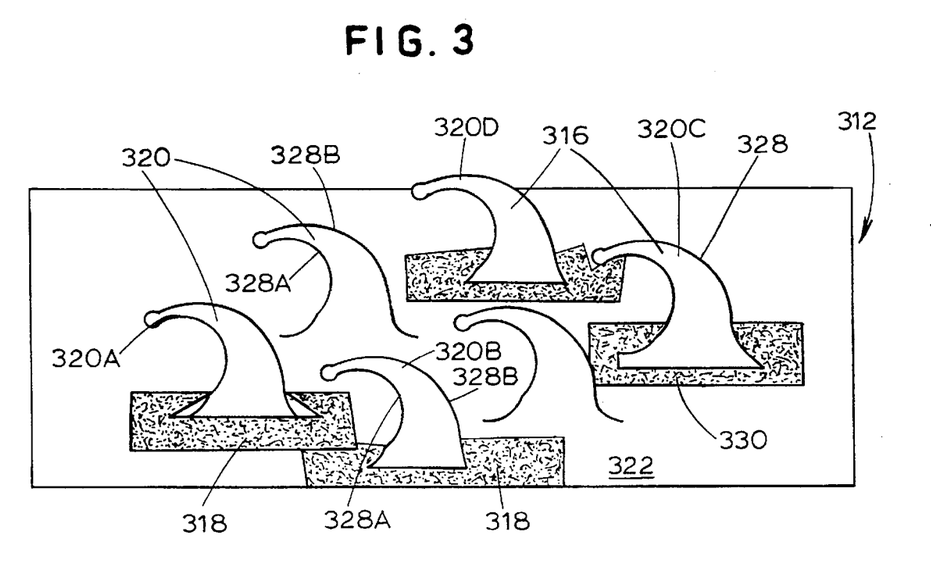
FIG. 3 is a schematic of a second embodiment of a first fastener portion of the present invention.
Figure 4:
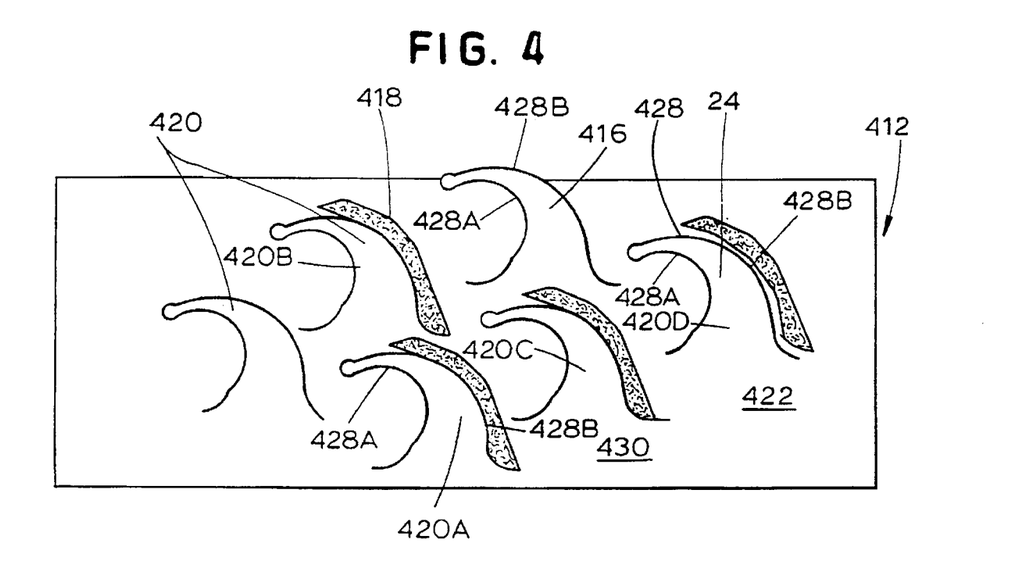
FIG. 4 is a schematic of a third embodiment of a first fastener portion of the present invention.
Figure 5:
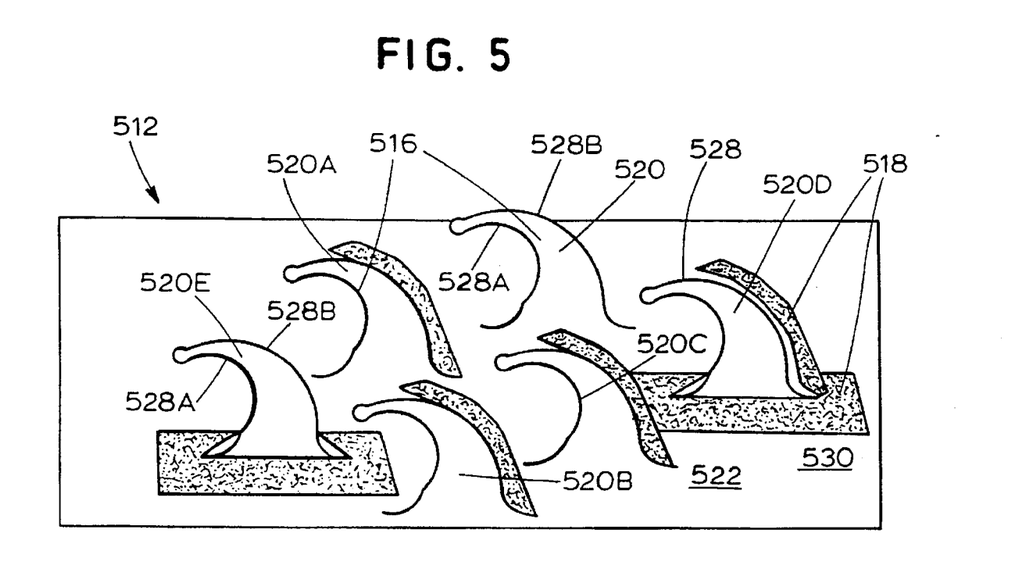
FIG. 5 is a schematic of a fourth embodiment of a first fastener portion of the present invention.

As seen in FIGS. 3–5, the cohesive portion 318, 418, 518 of the first fastener portion 312, 412, 512 may also be coated on a portion of the hook fastening material 316, 416, 516. As seen in FIGS. 3–5, the hook fastening material 316, 416, 516 has a hook surface area 328, 428, 528 and a base surface area 330, 430, 530. The hook surface area 328, 428, 528 is the surface of the engaging elements 320, 420, 520 of the hook fastening material 316, 416, 516. The hook surface area 328, 428 and 528 has a portion 328A, 428A, 528A which faces or is oriented towards the backing 322, 422, 522 and a portion 328B, 438B, 528B which is oriented away from or faces away from the backing 322, 422, 522. The base surface area 330, 430, 530 is the surface of the backing 322, 422, 522 from which the engaging elements 320, 420, 520 project.

As seen in FIG. 3, an embodiment of the first fastener portion 312 where a portion of the hook fastening material 316 is coated with cohesive 318 is provided. In this embodiment, only a portion of the base surface area 330 of the hook fastening material 316 is coated with cohesive 318. Although only a portion of the base surface area 330 is coated with cohesive 318 in FIG. 3, the entire base surface area 330 may be coated.

As seen in FIG. 4, another coated hook fastening material embodiment of the first fastener portion 412 is provided. This embodiment includes a portion of the hook surface area 428 of engaging elements 420A–420D of the hook fastening material 416 being coated with the first cohesive portion 418.

As seen in FIG. 5, a third coated hook fastening material embodiment of the first fastener portion 512 is provided. This embodiment includes at least a portion of both the hook surface area 528 of engaging elements 520A–D and a portion of the base surface area 530 by where engaging elements 520D–520E of the hook fastening material 516 project being coated with cohesive 518.

As seen in FIGS. 4 and 5 those engaging elements 420, 520 which are respectively coated with the first cohesive portion 418, 518 are coated only on the portions 428B, 528B of the hook surface area 428, 528 which are oriented away from the backing 422, 522 or base surface area 430, 530. Additionally or alternatively and depending on the composition of the receiving material, the entire surface area 428, 528 of the engaging elements 420, 520 may be coated or only the surface area 428A, 528A of the engaging elements 420, 520 which is oriented towards or faces the backing 422, 522 or base surface area 430, 530 may be coated with the first cohesive portion 418, 518.

To engage the primary fastener system 10, the first fastener portion 12 is brought in contact with the second fastener portion 14 wherein pressure exerted by the user activates a cohesive fastening mechanism comprised of the first and second cohesive portions 18 and 26 and a mechanical fastening mechanism comprised of the hook fastening material 16 and the receiving material 24. The pressure exerted by the user engages the cohesive mechanism by bonding or engaging the first cohesive portion 18 to the second cohesive portion 26 and activates the mechanical fastener mechanism by engaging the hook fastening material 16 to the receiving material 24.

Rather than requiring each of the two fastener mechanisms to individually provide the necessary peel and shear force resistances, the present invention utilizes and requires both of these two fastening mechanisms in combination to provide an engaged fastener with the desired shear force and peel force resistance. As used herein, "shear force resistance" is defined as the maximum force in the x/y plane, defined by the plane of the fastening mechanism, that the engaged fastening mechanism can withstand without disengaging. As used herein, "peel force resistance" is the maximum peel force in the z direction, the direction normal to the plane of the fastening mechanism, that the engaged fastener can withstand without disengaging. As discussed above, the mechanical fastener mechanism includes the hook fastening material 16 and the non-woven material 24. When there is sufficient tension between the hook fastening material 16 and the nonwoven in the x/y plane, the mechanical fastener mechanism provides excellent shear force resistance. Since the present invention allows the utilization of common inexpensive non-loop type receiving material 24, the mechanical fastener mechanism alone does not always provide adequate peel force resistance when there is little or no tension on the mechanical fastener mechanism in the x/y plane. In many instances, the mechanical fastener mechanism alone would disengage if there was not adequate x/y plane tension because the receiving material does not provide adequate anchors to which the hook fastening material could engage in the z direction.

The cohesive fastening mechanism, however, provides the fastener system 10 with the required peel force resistance that the mechanical fastener mechanism may not always provide and maintains the attachment of the fastener during times when there is lack of x/y plane tension. The cohesive fastener mechanism also provides some shear force resistance as well.

However, since the mechanical fastener mechanism provides shear force resistance, the cohesive fastener mechanism is not required to provide as much shear force resistance as it would if it was the sole fastener mechanism. This allows the use of weaker cohesives and smaller amounts of cohesive thereby preventing the destruction of the fastener mechanism or the materials to which the mechanism is attached to when the fastener system 10 is disengaged.

By having two mechanisms whose attributes can be altered, the proper shear and peel force resistances of the engaged fastener can be attained in a variety of ways. For example, the amount, type, and manner of applying the cohesive can be varied. Using cohesive with stronger bond strengths will increase the shear and peel force resistance. Also increasing the coat weight, i.e. the amount of the cohesive coated on the hook fastening material 16 and the receiving material 24 will increase the shear and peel forces. Typical cohesive coat weights are from 0.30 mg/in$^2$ to 1.0 g/in$^2$. Finally, the larger the surface area coated by the first and second cohesive portions 18 and 26, the greater amount of bond sites or contact points there will be between the two cohesive portions, and the greater the shear and peel force resistance will be.

Also, if the receiving material is a nonwoven material, its basis weight can be varied. A lower basis weight nonwoven material will allow the engaging elements 20 of the hook fastening material 16 to penetrate a deeper depth into the nonwoven receiving material 24. This will provide a strong shear force resistance as engaging elements 20 have more fibrous contact that prevents movement in the x/y plane. A lower basis weight, however, will provide the mechanical fastener mechanism with less peel force resistance because there is more space between the fibers and therefore less fibers for the engaging elements 20 of the hook fastener material 16 to engage in the z direction. As discussed above, for such a low basis weight nonwoven material, the cohesive mechanism would be used to provide the necessary additional peel force resistance.

The present invention can provide an engaged refastenable primary two mechanism fastening system having shear force resistance values greater than about 2000 g/in$^2$, preferably greater than 5000 g/in$^2$ and peel force resistance values between about 300 g/in$^2$ to about 2000 g/in$^2$, preferably 300–500 g/in$^2$, but always less than 5000 g/in$^2$.

Shear force resistance is measured by cutting a first representative sample of the first fastener portion and a second representative sample of the second fastener portion and following the method described in U.S. Pat. No. 4,699,622 to Toussant et al. which is incorporated herein by reference.

Peel force resistance is measured by cutting representative first and second samples, from the first and second fastener portions, respectively, and following the method described in U.S. Pat. No. 4,846,815 to Scripps which is incorporated herein by reference.

Fastening systems of the present invention have been found to be particularly useful and beneficial when applied to disposable absorbent articles. As used herein, the term "disposable absorbent article" refers to articles which absorb and contain body exudate; and, more specifically, refers to articles which are placed against or in proximity to the body of the wearer to absorb and contain the various exudates discharged from the body and which are intended to be discarded after a single use (i.e. they are not intended to be laundered or otherwise restored or reused). Examples of suitable disposable absorbent articles include diapers, incontinent briefs and undergarments, sanitary napkins, bibs, bandages, and the like.

Figure 6:
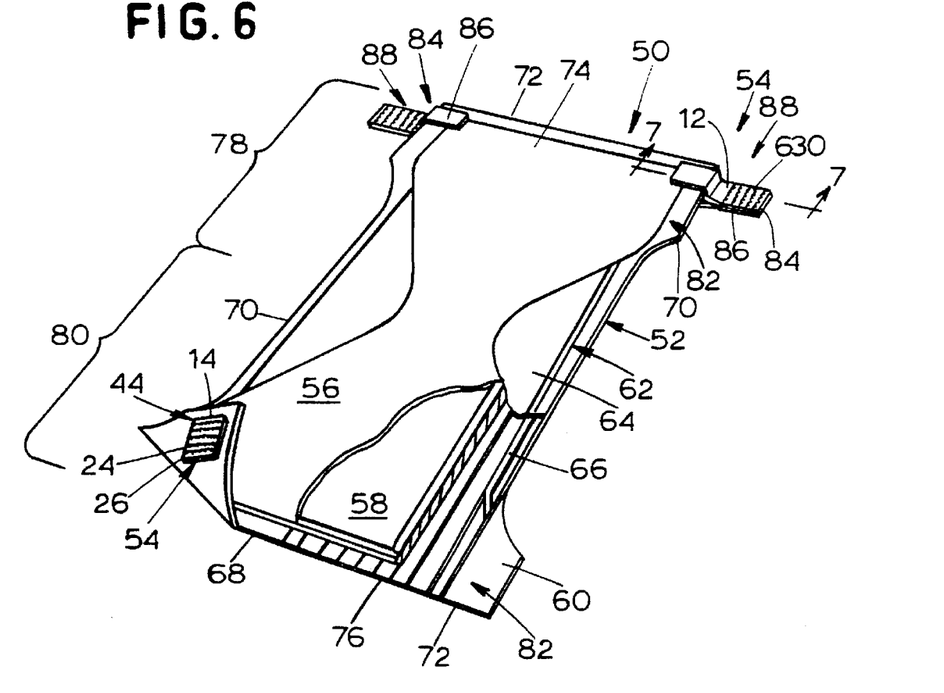
FIG. 6 is a partially cut-away perspective view of a diaper embodying the two-mechanism fastening device of the present invention.

A preferred embodiment of a disposable absorbent article embodying the present invention is shown in FIG. 6 as a diaper 50. As used herein, the term "diaper" refers to a garment generally worn by infants or incontinent persons that is drawn up between the legs and fastened about the waist of the wearer. Examples of the kinds of diapers to which the present invention is very readily adapted are shown in U.S. Pat. No. Re. 26,151 entitled "Disposable Diaper" which reissued to Robert C. Duncan and Norma L. Baker on Jan. 31, 1967; in U.S. Pat. No. 3,860,003 entitled "Contractable Side Portions For Disposable Diaper" which issued to Kenneth B. Buell on Jan. 14, 1975; and in U.S. Pat. No. 4,834,735 entitled "High Density Absorbent Members Having Lower Density and Lower Basis Weight Acquisition Zones" which issued to Miguel Alemany and Charles J. Berg on May 30, 1989, the disclosures of which are incorporated herein by reference. It will be apparent from the following description that the fastening system illustrated and described herein may be applied to the body portion of such diapers. On the other hand, it will be understood the invention is not limited to any specific diaper structure or configuration.

FIG. 6 is a partially cut-away perspective view of a diaper 50 embodying the present invention prior to it being placed on the wearer by the diaper user. As can be seen in FIG. 6, a preferred diaper 50 comprises a body portion 52 and a fastening system 54.

A preferred body portion 52 comprises a liquid pervious topsheet 56, an absorbent core 58, a liquid impervious backsheet 60, and elastically contractible leg cuffs 62, each leg cuff preferably comprising a side flap 64 and one or more elastic members 66. While the topsheet 56, the absorbent core 58, the backsheet 60, the side flaps 64, and the elastic members 66 may be assembled in a variety of well known configurations, a preferred disposable diaper configuration is shown and described generally in the above-referenced U.S. Pat. No. 3,860,003 which issued to Kenneth B. Buell on Jan. 14, 1975, and which patent is incorporated herein by reference. In this preferred diaper configuration, the backsheet 60 is joined with the topsheet 56; the absorbent core 58 is positioned between the topsheet 56 and the backsheet 60; the side flap 64 extends outwardly from and along each side edge of the absorbent core 58; and the elastic member 66 is operatively associated with each side flap 64.

FIG. 6 shows the body portion 52 in which the topsheet 56 and the backsheet 60 are coextensive and have length and width dimensions generally larger than those of the absorbent core 58. The topsheet 56 is superposed on the backsheet 60 thereby forming the periphery 68 of the body portion 52, in other words, the outer extent of the body portion 52. The periphery 68 comprises longitudinal edges 70 and end edges 72.

The body portion 52 has an inside surface 74 and an outside surface 76. In general, the outside surface 76 of the diaper 50 extends from one end edge 72 to the other end edge 72 of the diaper 50 and from one longitudinal edge 70 to the other longitudinal edge 70 of the diaper 50 and is the surface farthest from the wearer during use of the diaper 50. When a backsheet 60 is used, it typically forms the outside surface 76 of the body portion 52. The inside surface 74 is that surface of the diaper 50 opposite the outside surface 76 and in the embodiment shown is typically formed by the topsheet 56. In general, the inside surface 74 of the diaper 50 is that surface coextensive with the outside surface 76 and which is for the greater part in contact with the wearer when the diaper 50 is worn.

The diaper 50 has a first end region 78 and a second end region 80 extending from the end edges 72 of the diaper periphery 68 toward the lateral centerline of the diaper 50. Both the first end region 78 and the second end region 80 extend a distance of about one-half the length of the diaper 50 such that the end regions comprise each half of the diaper 50.

Both the first end region 78 and the second end region 80 have panels 82. The panels 82 are those portions of the first end region 78 and the second end region 80 which overlap when the diaper 50 is fastened about the waist of the wearer. The extent to which the end regions overlap and thus the extent to which the panels 82 are formed, will depend on the overall dimensions and shape of the diaper 50 and the size of the wearer.

The diaper 50 is provided with a fastening system 54 for forming a side closure. Thus, the diaper 50 is fitted to the wearer and the panels 82 of the first end region 78 and the second end region 80 are maintained in an overlapping configuration when the diaper 50 is worn.

Figure 7:
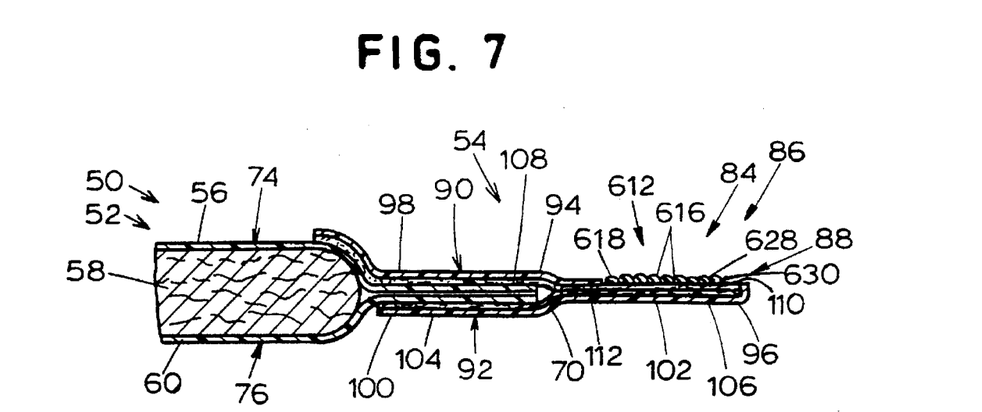
FIG. 7 is an enlarged fragmentary sectional view taken along 7—7 of FIG. 6.

In a preferred embodiment of the present invention as shown in FIG. 6, the fastening system 54 comprises a closure member 84 disposed adjacent each longitudinal edge 70 of the body portion 52 in the first end region 78, and a landing member 44 disposed on the outside surface 76 of the body portion 52 in the second end region 80. As shown in FIG. 6, the closure member 84 preferably comprises a tape tab 86 and a first fastener portion 612 of the present invention (a first fastening element 88) comprising a hook fastening material 616 and a first cohesive portion 618. As described above, the hook fastening material 616 has a hook surface area 628 and a base surface area 630. As shown in FIGS. 6 and 7, a portion of both the hook and base surface area 628 and 630 are coated with cohesive 618. In addition, as described above, the first cohesive portion 618 may also be segregated from the hook fastening material or may be coated on a portion of the hook fastening material 616 as shown in FIGS. 2–5.

The landing member 44 which is engageable with the first fastening element 88 is comprised of the second fastener portion 14 of the present invention, as seen in FIG. 1, a nonwoven fibrous material 24 coated with a cohesive material 26.

Each closure member 84 is intended to provide a fastening means for engaging the landing member 44 so as to provide a secure side closure for the diaper 50. Thus, the closure member 84 comprises at least the first fastening element 88. Each closure member 84 also preferably comprises a means for positioning the first fastening element 88 adjacent the landing member 44 so as to achieve a side closure. Thus, the closure member 84 may comprise any of the well known configurations and securement means for achieving a side closure on a diaper 50 such as an inner fastening member secured to the inside surface 74 and/or the outside surface 76 of the body portion 52, tape tabs, or belts. An exemplary embodiment of an inner fastening member is described in U.S. Pat. No. 4,699,622 entitled "Disposable Diaper Having An Improved Side Closure" issued to John W. Toussant and Margaret H. Hasse on Oct. 13, 1987, which patent is incorporated herein by reference. An embodiment of an incontinent undergarment using a belt suspension system is disclosed in U.S. Pat. No. 4,315,508 entitled "Self-Centering Multiple Use Garment Suspension System" issued to Bolick on Feb. 16, 1982, incorporated herein by reference.

As shown in FIG. 6, each closure member 84 most preferably comprises a tape tab 86. Any of the well known configurations and constructions of a tape tab 86 may be used. A preferred tape tab 86 is a Y-shaped tape tab as described in detail in U.S. Pat. No. 3,848,594 entitled "Tape Fastening System for Disposable Diaper" which issued to Kenneth B. Buell on Nov. 19, 1974 and which patent is incorporated herein by reference. As shown in FIG. 6, a tape tab 86 is provided on both longitudinal edges 70 of the body portion 52, most preferably in the first end region 78.

A particularly preferred tape tab 86 is illustrated in FIG. 7 and has a tab fastening surface 90 and a tab backing surface 92. The tab fastening surface 90 is that surface of the tape tab 86 designed to engage the landing member 44 of the present invention. Thus, the tab fastening surface 90 of the tape tab 86 will generally correspond to the inside surface 74 of the body portion 52. The tab backing surface 92 is that surface opposite of the tab fastening surface 90 and generally corresponds to the outside surface 76 of the body portion 52. The tab backing surface 92 is thus generally exposed during wear of the diaper 50.

The preferred tape tab 86 illustrated in FIG. 7 is one which is anchored to both the inside surface 74 and the outside surface 76 of the body portion 52 to create a fixed end 94 (i.e., that attachment of the tape tab 86 to the diaper 50 made during manufacture of the diaper 50). The tape tab 86 has another element which forms the tab end 96 (i.e that joint made by the person in securing the diaper 50 to the wearer) that is secured to the fixed end 94 and extends beyond the longitudinal edge 70 of the body portion 52 so as to be secured to the landing member 44. Thus, the preferred tape tab 86 of the present invention has at least three elements, a first fixed portion 98, a second fixed portion 100, and a connective portion 102. The first fixed portion 98 is that portion of the tape tab 86 which is attached to the inside surface 74 of the body portion 52. The second fixed portion 100 is that portion of the tape tab 86 which is attached to the outside surface 76 of the body portion 52. The first fixed portion 98 and the second fixed portion 100 thus form the fixed end 94 of the tape tab 86. The connective portion 102 is that portion of the tape tab 86 which is attached to anther portion of the diaper 50, generally the landing member 44, by the user when securing the diaper 50 on the wearer. The connective portion 102 thus forms the tab end 96. Additionally, the outer surface 104 of the second fixed portion 100 and the outer surface 106 of the connective portion 102 form the tab backing surface 92 of the tape tab 86 while the inner surface 108 of the first fixed portion 98 and the inner surface 110 of the connective portion 102 form the tab fastening surface 90 of the tape tab 86.

The preferred Y-shaped tape tab 86 of the present invention can be constructed in several ways. The first fixed portion 98, the second fixed portion 100, and the connective portion 102 can each be separate tapes which meet and are joined adjacent the longitudinal edge 70 of the body portion 52 in an area of joinder. A more practical structure for the tape tab 86 is one in which the connective portion 102 and either the first fixed portion 98 or the second fixed portion 100 are a unitary strip of tape material. If the connective portion 102 is unitary with the second fixed portion 100 as shown in FIG. 7, then the first fixed portion 98 is a separate element which is attached to the combined connective portion and the second fixed portion adjacent to the longitudinal edge 70 of the body portion 52.

Preferred materials for the tape tabs comprise a tape material such as tape code number XPF14.43.0, Y-9376, or Y-9030 available from The Minnesota Mining and Manufacturing Company, of St Paul, Minn. The tape material in the embodiments are preferably a polyethylene film having a tab attachment means tailored to bond to the polyethylene positioned on the tape material. The tab attachment means may comprise any of these adhesives which provide an adequate bond with other portions of the diaper 50 and is preferably any of the pressure-sensitive adhesives well-known to those of ordinary skill in the art. Preferred tab attachment means is a pressure-sensitive adhesive such as Code Number XPF1.42.34 available from The Minnesota Mining and Manufacturing Company, of St. Paul, Minn.

The first fastening element 88 of the closure member 84 forms the closure between the closure member 84 and the landing member 44. Thus, the first fastening element 88 provides elements that engage the nonwoven fibrous material 24 that is coated with cohesive 26 of the landing member 44 to maintain the first end region 78 and the second end region 80 in an overlapping configuration to provide a secure side closure. The first fastening element 88 comprises the first fastener portion 612 of the present invention having a hook fastening material 616 that is coated with cohesive 618.

The first fastening element 88 may be a separate member joined to and associated with the closure member 84 or a unitary member with the closure member 84.

The first fastening element 88 is preferably joined to either the body portion 52 or the tape tab 86. As used herein, the term "joined" encompasses configuration whereby the first fastening element 88 is releasably secured to the diaper 50 so the first fastening element 88 may be removed from the diaper 50 or its location during use and whereby the first fastening element 88 is affixed to the diaper 50 such that the first fastening element 88 is securely fastened to the diaper 50. Joined is also used to denote that the first fastening element 88 may be directly joined to the diaper 50 or may be indirectly joined to the diaper 50 such as by releasably securing or affixing the first fastening element 88 to an intermediate member which is in turn is releasably secured or affixed to the diaper 50. Preferably, as shown in FIG. 6, the first fastening element 88 is directly affixed to the connective portion of the tape tab 86 by a second tab attachment means 112.

In addition, the first fastening element 88 may be positioned anywhere on the diaper 50. When the closure member 84 comprises an inner fastening member, the first fastening element 88 is preferably positioned in the panels 82 of the first end region 78 adjacent the longitudinal edges 70. When the closure member 84 comprises a tape tab 86, the first fastening element 88 is preferably positioned either on all of or at least a portion of the fastening surface 90, or preferably on all of or at least a portion of the connective portion 102. Most preferably, the first fastening element 88 is disposed on the connective portion 102 on the fastening surface 90 of the tape tab 86.

The landing member 44 of the fastening system 54 provides a means for securing itself and the closure member 84 together to provide a secure side closure and to maintain the first end region 78 and the second end region 80 in an overlapping configuration. The landing member 44 may be disposed anywhere on the diaper 50 so long as it engages the closure member 84 so as to provide the side closure. For example, the landing member 44 may be disposed on the outside surface 76 in the second end region 80, on the inside surface 74 in the first end region 78, or on any other portion of the diaper 50 which is dispomember engage the closure member 84. In addition, the landing member 44 may either be a discrete separate element affixed to an element of the diaper 50 (such as the topsheet 56 or the backsheet 60) or a unitary piece of material that is neither divided nor discontinuous with an element of the diaper 50 such as the topsheet 56 or the backsheet 60. While the landing member 44 can assume varying sizes and shapes, it preferably comprises one or more (at least one) separate patches of material that are larger in area than the first fastening element 88 and which are secured to the body portion 52 to allow for a maximum fit adjustment at the waist of the wearer. The preferred embodiment of the diaper 50 illustrated in FIG. 6 has a rectangular-shaped landing member 44 secured to the outside surface 76 of the body portion 52 in the panels 82 of the second end region 80 adjacent each of the longitudinal edges 70.

In use, the diaper 50 is applied to the wearer by positioning the first end region 78 under the wearer's back and drawing the remainder of the diaper 50 between the legs of the wearer so the second end region 80 is positioned across the front of the wearer. The connective portion 102 of the tape tabs 86 are then positioned adjacent to the landing member 44 positioned on the outside surface 76 of the second end region 80 so the hook fastening material 616 and the cohesive 618 of the first fastener portion 612 of the first fastening element 88 which is disposed on the fastening surface 90 of the tape tab 86 will respectively engage the nonwoven material 24 and the cohesive material 26 of the landing member 44 to form a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A primary two mechanism fastening system capable of being unfastened without rendering the system unrefastenable comprising:
   a first fastener portion comprising
   (i) a hook fastening material having a base surface area and a hook surface area
   (ii) a first cohesive portion coated on at least a portion of said hook fastening material; and
   a second fastener portion comprising
   (i) a receiving material engageable with said hook fastening material wherein said receiving material is a nonwoven,
   (ii) a second cohesive portion coated on at least a portion of said receiving material engageable with said first cohesive portion, whereby when said first and second fastener portions are engaged, said first and second cohesive portions are bonded together.

2. The primary fastening system of claim 1 wherein said first cohesive portion is coated on at least a portion of said hook surface area.

3. The primary fastening system of claim 1 wherein said first cohesive portion is coated on said base surface area of said hook fastening material.

4. The primary fastening system of claim 3 wherein said first cohesive portion is coated on both said hook surface area and said base surface area of said hook fastening material.

5. The primary fastening system of claim 2 wherein said hook surface area includes a surface area portion oriented towards said base surface area and coated with said first cohesive portion.

6. The primary fastening system of claim 2 wherein said hook surface area includes a surface area portion oriented away from said base surface area and coated with said first cohesive portion.

7. The primary fastening system of claim 1 wherein said primary fastening system has a shear strength of at least about 2000 g/in$^2$ and a peel strength of not more than about 5000 g/in$^2$ when said first mechanical and cohesive portions are engaged with said respective second mechanical and cohesive portions.

* * * * *